United States Patent [19]
Bauer et al.

[11] Patent Number: 6,034,123
[45] Date of Patent: *Mar. 7, 2000

[54] METHOD FOR ALTERING BLOOD LIPID LEVELS

[75] Inventors: Carl-Axel Wilhelm Edvard Bauer; Leif Åke Svensson, both of Lund, Sweden

[73] Assignee: Astra Aktiebolag, Sodertalje, Sweden

[*] Notice: This patent is subject to a terminal disclaimer.

[21] Appl. No.: 09/193,940

[22] Filed: Nov. 17, 1998

Related U.S. Application Data

[63] Continuation of application No. 07/670,053, Mar. 15, 1991, Pat. No. 5,837,727.

[30] Foreign Application Priority Data

Mar. 16, 1990 [SE] Sweden .................................. 9000948

[51] Int. Cl.⁷ .................................................. A61K 31/27
[52] U.S. Cl. ........................................... 514/483; 514/824
[58] Field of Search ...................... 514/483, 824

[56] References Cited

U.S. PATENT DOCUMENTS

| | | | |
|---|---|---|---|
| 4,419,364 | 12/1983 | Olsson et al. | 424/300 |
| 4,472,436 | 9/1984 | Hooper | 514/653 |
| 5,837,727 | 11/1998 | Bauer et al. | 514/483 |

FOREIGN PATENT DOCUMENTS

| | | |
|---|---|---|
| 0043807 | 1/1982 | European Pat. Off. . |
| 0244062 | 11/1987 | European Pat. Off. . |

OTHER PUBLICATIONS

Tunek, et al., Chem. Abstracts 110:18381z, p. 46 (1989).
Jain, et al., Clin. Chem. 29:1031–1033 (1983).
Tunek, et al., Drug Metabolism and Disposition 16:759–764 (1988).
Hooper, et al., New England J. Med. 305:1455–1457 (1981).

*Primary Examiner*—Kimberly Jordan
*Attorney, Agent, or Firm*—White & Case LLP

[57] ABSTRACT

Use of bambuterol or a pharmaceutically acceptable salt thereof for the manufacture of a pharmaceutical preparation with lipid lowering effect.

14 Claims, No Drawings

METHOD FOR ALTERING BLOOD LIPID LEVELS

This application is a continuation of Application Ser. No. 07/670,053, filed Mar. 15, 1991, which issued as U.S. Pat. No. 5,837,727 on Nov. 17, 1998.

FIELD OF THE INVENTION

The present invention is related to the use of a pharmaceutically acceptable salt of the bis-dimethyl carbamate prodrug of terbutaline, namely 5-[2-(tert-butylamino)-1-hydroxyethyl]-m-phenylene-bis(dimethylcarbamate), called bambuterol or a pharmaceutically acceptable salt thereof in the manufacture of pharmaceutical preparations with lipid lowering effects.

BACKGROUND OF THE INVENTION

Bambuterol, which is described in the European patent EP 43807 is a pro drug of a beta-2-adrenergic agonist (terbutaline) and can be used in the treatment of asthmatic patients, no effect on the lipoprotein metabolism has been reported earlier.

A positive correlation between high risk for coronary heart disease and increased concentrations of low-density lipoprotein (LDL) has been well documented, Castelli W P, Doyle J T, Gordon T, et al. HDL Cholesterol and other lipids in coronary heart disease. The Cooperative Lipoprotein Phenotyping Study. Circulation 55, 767–772 (1977). In contrast, it has been suggested that an increased concentration of high-density lipoprotein (HDL) may confer a low risk for heart disease. A more recent study, Gordon T, Castelli W P, Hjortland M C, et al. High density lipoprotein as a protective factor against coronary heart disease. The Framingham Study. Am J Ned 62, 707–714 (1977), however, suggests that the ratio between LDL cholesterol and HDL Cholesterol is a better indicator of risk rather than either of them alone, on the premise that LDL transports the cholesterol produced in the liver to the extra-hepatic tissues and HDL brings it back into the liver for further metabolism.

Different kinds of cholesterol are present in the blood, and the most important forms are HDL= High Density Lipoprotein, and LDL= Low Density Lipoprotein.

PRIOR ART

In an earlier study the beta-2-adrenoreceptor agonist terbutaline was found to significantly increase the HDL-cholesterol levels in healthy nonobese man. Cf Hooper P. L et al N.Engl.J.Med 305, p. 1455, 1981. Furthermore, it is known from Jain R et al. Clin. Chem 29, p. 1031, 1983 that there might be an interrelationship between plasma cholinesterase inhibition and lipoprotein metabolism, resulting in a decrease in LDL cholesterol. There is, however, always a risk with plasma cholinesterase inhibition, namely if the effect is not selective towards the plasma cholinesterase. An unselective inhibitor gives toxic effects depending on the inhibition of acetylcholinesterase. Thus in order to obtain an effective lipid lowering effect, the combination of a HDL-cholesterol increasing effect and a plasma cholinesterase inhibiting effect, which will lower LDL, is wanted.

OUTLINE OF THE INVENTION

With the background above it was decided to test the lipid lowering effect of bambuterol, which is a specific inhibitor of plasma cholinesterase, which generates the beta-2-adrenoreceptor agonist terbutaline, which gives a significantly prolonged duration of effect of 24 h versus 8 h for conventional terbutaline tablets or 12 h for terbutaline slow release tablets (compared to terbutaline). The lipid lowering preparation contains between 5–30 mg of bambuterol, preferably 10–20 mg. It is especially preferred to use the hydrochloride of bambuterol. The pharmaceutical preparations are preferably in the form of tablets, but it is also possible to use other kinds of preparations such as capsules, oral solutions or injection solutions.

Conventional pharmaceutical preparations can be used.

BIOLOGICAL TEST

In a study on the effects of bambuterol and terbutaline slow release on lipoprotein metabolism in healthy volunteers with normal lipoprotein status both bambuterol and terbutaline induced favourable changes in lipoprotein metabolism, and atherogenic index (s-LDL/s-HDL), statistically significant and clinically relevant elevations were seen in HDL cholesterol and Apo A1 concentrations (in Apo A1 the major protein component is HDL), while plasma triglycerides levels decreased. In parallel the activity of lipoprotein lipase increased suggesting that the alterations in plasma lipoprotein concentrations were mediated via an increase in the rate of turnover of triglyceride-rich lipoproteins. No effect on LDL cholesterol could be demonstrated with any of the drugs.

On the other hand, in a second placebo controlled study in 16 patients with diabetes mellitus with moderately impaired lipoprotein status, bambuterol 20 mg once daily for 6 weeks was found to significantly rise S-HDL-cholesterol levels and to lower S-LDL-cholesterol levels compared to placebo. This was accompanied by a significant decrease in both S-cholesterol and S-triglyceride levels. Cf Table 1.

TABLE 1

Effects of bambuterol on lipoprotein metabolism markers in 16 diabetes mellitus patients.

|  | Before treatment | After 3 weeks | After 6 weeks | N = 16 |
| --- | --- | --- | --- | --- |
| S-HDL-Cholesterol (mmol/L) | 1.06 ± 0.31 | P: 1.12 ± 0.34<br>B: 1.29 ± 0.35 | 1.18 ± 0.33<br>1.26 ± 0.35 | p = 0.0001 |
| S-LDL-Cholesterol (mmol/L) | 4.04 ± 0.92 | P: 4.11 ± 0.89<br>B: 3.85 ± 0.98 | 4.11 ± 0.93<br>3.90 ± 0.97 | p = 0.004 |
| S-Cholesterol | 5.92 ± 1.08 | P: 6.02 ± 0.93 | 6.00 ± 0.89 | p = 0.029 |

TABLE 1-continued

Effects of bambuterol on lipoprotein metabolism markers in 16 diabetes mellitus patients.

|  | Before treatment | After 3 weeks | After 6 weeks | N = 16 |
|---|---|---|---|---|
| (mmol/L) |  | B: 5.76 ± 1.14 | 5.78 ± 1.05 |  |
| S-Triglyceride | 1.86 ± 1.62 | P: 1.69 ± 1.10 | 1.58 ± 0.98 | p = 0.026 |
| (mmol/L) |  | B: 1.38 ± 0.86 | 1.36 ± 0.86 |  |

P = Placebo
B = Bambuterol

CONCLUSION

From the results given in table 1, it can be concluded that bambuterol gives beneficial effects on the lipoprotein metabolism in patients with moderately impaired lipoprotein status. The effect of bambuterol is persistent and highly significant and of the same order as seen with other well known lipid lowering drugs. Bambuterol thus offers a new, convenient lipid lowering therapy, since bambuterol is dosed only once daily.

We claim:

1. A method of treating a human subject with impaired lipoprotein status so as to lower the subject's blood lipid levels, which comprises orally administering to a subject in need of such treatment an amount of bambuterol or a pharmaceutically acceptable salt thereof sufficient to lower the subject's blood lipid levels.

2. A method according to claim 1, wherein the hydrochloride of bambuterol is the pharmaceutically acceptable salt.

3. A method according to claim 1 or 2, wherein the amount of bambuterol or a pharmaceutically acceptable salt thereof is in the dosage range of 5 mg to 30 mg.

4. A method according to claim 3, wherein the dosage range is 10 mg to 20 mg.

5. A method according to claim 1 or 2, wherein the human subject has an impaired lipoprotein status as evidenced by a high atherogenic index.

6. A method for altering the lipoprotein status, as evidenced by lowering the atherogenic index, of a human subject with impaired lipoprotein status, which comprises orally administering to a subject in need of such treatment an amount of bambuterol or a pharmaceutically acceptable salt thereof sufficient to lower the subject's atherogenic index.

7. A method according to claim 6, wherein the hydrochloride of bambuterol is the pharmaceutically acceptable salt.

8. A method according to claim 6 or 7, wherein the amount of bambuterol or a pharmaceutically acceptable salt thereof is in the dosage range of 5 mg to 30 mg.

9. A method according to claim 8 wherein the dosage range is 10 mg to 20 mg.

10. A method of treating a human subject with impaired lipoprotein status so as to raise the subject's S-HDL-cholesterol levels and lower the subject's S-LDL-cholesterol levels, which comprises orally administering to a subject in need of such treatment an amount of bambuterol or a pharmaceutically acceptable salt thereof sufficient to raise the subject's S-HDL-cholesterol levels and lower the subject's S-LDL-cholesterol levels.

11. A method according to claim 10, wherein the hydrochloride of bambuterol is the pharmaceutically acceptable salt.

12. A method according to claim 10 or 11, wherein the amount of bambuterol or a pharmaceutically acceptable salt thereof is in the dosage range of 5 mg to 30 mg.

13. A method according to claim 12, wherein the dosage range is 10 mg to 20 mg.

14. A method of treating coronary heart diseases, atherosclerosis and/or lipoprotein metabolic disorders in a human subject, which comprises orally administering to a subject in need of such treatment a therapeutically effective amount of bambuterol or a pharmaceutically acceptable salt thereof.

* * * * *